US011078169B2

(12) United States Patent
Feraud et al.

(10) Patent No.: US 11,078,169 B2
(45) Date of Patent: Aug. 3, 2021

(54) METHOD FOR PREPARING 3,7-BIS(DIMETHYLAMINO)PHENOTHIAZIN-5-YLIUM IODIDE

(71) Applicant: PROVEPHARM LIFE SOLUTIONS, Marseilles (FR)

(72) Inventors: Michel Feraud, Marseilles (FR); Babak Sayah, Marseilles (FR); Stéphane Queru, Marseilles (FR); Marina Laurent, Marseilles (FR)

(73) Assignee: PROVEPHARM LIFE SOLUTIONS, Marseilles (FR)

( * ) Notice: Subject to any disclaimer, the term of this patent is extended or adjusted under 35 U.S.C. 154(b) by 0 days.

(21) Appl. No.: 16/490,480

(22) PCT Filed: Feb. 16, 2018

(86) PCT No.: PCT/FR2018/050372
§ 371 (c)(1),
(2) Date: Aug. 30, 2019

(87) PCT Pub. No.: WO2018/158520
PCT Pub. Date: Sep. 7, 2018

(65) Prior Publication Data
US 2020/0010438 A1 Jan. 9, 2020

(30) Foreign Application Priority Data
Mar. 2, 2017 (FR) ...................................... 1751700

(51) Int. Cl.
*C07D 285/15* (2006.01)
(52) U.S. Cl.
CPC .................. *C07D 285/15* (2013.01)
(58) Field of Classification Search
CPC combination set(s) only.
See application file for complete search history.

(56) References Cited

U.S. PATENT DOCUMENTS 10,472,340 B2 * 11/2019 Hecht .................. C07D 417/04

FOREIGN PATENT DOCUMENTS

| GB | 2373787 A | 10/2002 |
|---|---|---|
| WO | 03/082296 A1 | 10/2003 |
| WO | 2005/054217 A1 | 6/2005 |
| WO | 2006/032879 A2 | 3/2006 |
| WO | 2008/006979 A2 | 1/2008 |
| WO | 2008/007074 A2 | 1/2008 |

OTHER PUBLICATIONS

"Alzheimer's disease." CNN Health, Obtained Oct. 9, 2010, URL:http://www.cnn.com/2003/HEALTH/conditions/09/24/alzheimers.drug.ap/index.html.*

Antonio R. Damasio, Alzheimer's Disease and Related Dementias, Cecil Textbook of Medicine, 20th edition (1996), vol. 2, pp. 1992-1996.*
Strekowski et al; "A Synthetic Route to 3-(Dialkylamino)phenothiazin-5-ium Salts and 3,7-Disubstituted Derivatives Containing Two Different Amino Groups;" Journal of Heterocyclic Chemistry; Dec. 1993; 30; pp. 1693-1695.
Sep. 3, 2019 International Preliminary Report on Patentability issued in International Patent Application No. PCT/FR2018/050372.
Leventis et al; "Synthesis of Substituted Phenothiazines Analogous to Methylene Blue by Electrophilic and Nucleophilic Aromatic Substitutions in Tandem. A Mechanistic Perspective.;" Tetrahedron; 1997; vol. 53; No. 29; pp. 10083-10092.
Mellish et al; "In Vitro Photodynamic Activity of a Series of Methylene Blue Analogues;" Photochemistry and Photobiology; 2002; 75(4); pp. 392-397.
Gollmer et al; "A novel set of symmetric methylene blue derivatives exhibits effective bacteria photokilling—a structure-response study;" Photochemical & Photobiological Sciences; 2014; DOI:10/1039/C4PP00309H; also cited as Gollmer et al; Photochem. Photobiol. Sci.; vol. 14, n° 2, Jan. 1, 2015, p. 335-351.
"Methylthioninium Chloride;" European Pharmacopoeia; 2014-2016; vol. 8.6; pp. 5329-5331.
Jul. 16, 2018 International Search Report issued in International Patent Application No. PCT/FR2018/050372.
Cody, Jeremy, et al. "A convenient one-pot synthese of ethylene blue". Tetrahedron Letters, 2012, pp. 4896-4899.
Wischik, Claude, et al. "Tau-aggregation inhibitor therapy for Alzheimer's disease". Biochemical Pharmacology, 88, pp. 529-539, 2014.
Anthony, Melinda, et al. "The global pipeline of new medicines for the control and elimination of malaria". Malaria Journal, BioMed Central, 11:316, 2012.
Floyd, Robert, et al. "Methylene blue photoinactivation of RNA viruses". Science Direct, Antiviral Research, 61, pp. 141-151, 2004.
Fryk, Jesse, et al. "Dengue and chikungunya viruses in plasma are effectiely inactivated after treatement with methylene blue and visible light". Wiley, 2016.
Helfritz, Fabian, et al. "Methylene Blue Treatment of Grafts During Cold Ischemia Time Reduces the Risk of Hepatitis C Virus Transmission". The Journal of Infectious Diseases, Infectious Diseases Society of America, pp. 1711-1721, 2018.
Levin, Ricardo, et al. "Methylene Blue Reduces Mortality and Morbidity in Vasoplegic Patients After Cardiac Surgery". The Society of Thoracis Surgeons, pp. 496-499, 2004.
Rojas, Julio, et al. "Neurometabolic mechanisms for memory enhancement and neuroprotection of methylene blue". Prog Neurobiol., 96(1): 32-45, 2012.
Seltsam, Axel, et al. "Update on the use of pathogen-reduced human plasma and platelet concentrates". British Journal of Hematology, pp. 442-454, 2013.
Silva, Emmanuel, et al. "Evaluation of Photodynamic Therapy Using a Diode Laser and Different Photosensitizers Against Enterococcus Faecalis". Acta Odontol. Latinoam., vol. 27, pp. 63-65, 2014.

(Continued)

*Primary Examiner* — Alicia L Otton
(74) *Attorney, Agent, or Firm* — Oliff PLC

(57) ABSTRACT

Method for preparing 3,7-bis(dimethylamino)phenothiazin-5-ylium iodide, the method resulting in a high purity while being very simple to implement and producing high yields. The method uses phenothiazine as a starting material and includes the following steps: a) treating phenothiazine with diiodine, b) treating the reaction medium directly obtained from step a) with dimethylamine.

15 Claims, No Drawings

(56) References Cited

OTHER PUBLICATIONS

Khoury, Elizabeth, et al. "Daily consumption of methylene blue reduces attentional deficits and dopamine reduction in a 6-OHDA model of Parkinson's disease". Neuroscience, pp. 8-16, 2017.
Tucker, Donovan, et al. "From Mitochondrial Function to Neuroprotection—An Emerging Role for Methylene Blue". Mol Neurobiol., 55(6), pp. 5137-5153, 2018.
FDA notice of use for Provayblue, "Highlights of Prescribing Information" pp. 1-10, 2016.
Paban, V, et al. "Therapeutic and preventive effects of mehylene blue on Alzheimer's disease pathology in a transgenic mouse model". Science Direct, Neuropharmacology, pp. 68-79, 2014.
Pal, Rahul, et al. "Nonphotodynamic Roles of Methylene Blue: Display of Distinct Antimycobacterial and Anticandidal Mode of Actions". Hindawi Journal of Pathogens, pp. 1-14, 2018 (Article ID 3759704).
Poteet, Ethan, et al. "Neuroprotective Actions of Methylene Blue and Its Derivatives". PLOS One, pp. 1-17, vol. 7, Issue 10, Oct. 2012.
Mar. 19, 2020 Office Action issued in Indian Patent Application No. 201917036476.

* cited by examiner

METHOD FOR PREPARING 3,7-BIS(DIMETHYLAMINO)PHENOTHIAZIN-5-YLIUM IODIDE

The present invention relates to a novel process for preparing 3,7-bis(dimethylamino)phenothiazin-5-ylium iodide, this method making it possible to obtain a product with a high degree of purity, while at the same time being very simple to carry out and providing high yields. This method makes it possible to obtain other halides, in particular 3,7-bis(dimethylamino)phenothiazin-5-ylium chloride, in a few steps. Thus, this process constitutes the first step of a route for obtaining a methylene blue of high quality and with good yields.

PRIOR ART

Various processes for synthesizing phenothiazine derivatives, substituted in position 3 and position 7 with groups that may be identical or different are known from the prior art. The common factor in all these processes is that they are carried out in several steps.

The document "A synthetic Route to 3-(Dialkylamino) phenothiazin-5-ium Salts and 3,7-Disubstituted Derivatives Containing Two Different Amino Groups" (L. Strekowski, D. F. Hou and R. L. Wydra; *Journal of Heterocyclic Chemistry;* 1993; 30; 1693-1695) describes the preparation, in several steps, of phenothiazine derivatives substituted in positions 3 and 7 with distinct groups. The first step of this process consists in converting the phenothiazine into periodide, also known as phenothiazine-5-ylium tetraiodide, which is purified and isolated. The second step of this process consists in adding two molar equivalents of dialkylamine to the periodide, in order to obtain a phenothiazine derivative substituted in position 3 with a dialkylamine. A treatment with at least four molar equivalents of another dialkylamine makes it possible to obtain an asymmetric phenothiazine derivative substituted in positions 3 and 7. This process was adapted to the synthesis of 3,7-bis(dialkylamino)phenothiazin-5-ylium iodides by K. J. Mellish et al., Photochemistry and Photobiology, 2002, 75(4); 392-397, with $C_2$ to $C_6$ alkyls. This process calls upon the use of solvents such as chloroform, the industrial-scale use of which is not very desirable. In addition, the yields are at best 55%.

The document "A novel set of symmetric methylene blue derivative exhibits effective bacteria photokilling—a structure-response study" (Anita Gollmer, et al., Photochem. Photobiol. Sci.; vol. 14, n°2, 1 Jan. 2015, p. 335-351) is the only one to describe the multistep preparation of 3,7-bis(dimethylamino)phenothiazin-5-ylium chloride via 3,7-bis(dimethylamino)phenothiazin-5-ylium periodide. The first step of this process consists in converting the phenothiazine to periodide which is purified and isolated. The second step consists in treating the periodide with dimethylamine dissolved in a mixture of methanol and dichloromethane. An ion exchange makes it possible to obtain 3,7-bis(dimethylamino)phenothiazin-5-ylium chloride. No precise and reproducible procedure is disclosed. This process calls for the use of solvents such as dichloromethane, the industrial-scale use of which is not very desirable. When an attempt was made to reproduce this process, low yields (42.7%) and a product having a purity of 85.36% (HPLC) were obtained.

The document N. Leventis et al., Tetrahedron 1997 vol. 53, N° 29, 10083-10092, 1997 describes a two-step synthesis of 3,7-bis(dimethylamino)phenothiazin-5-ylium bromide: firstly, a treatment with a large excess of bromine in acetic acid makes it possible to form 3,7-bis(dibromo) phenothiazin-5-ylium bromide, followed by a treatment with dimethylamine. The first step of this process has numerous drawbacks: the use of a large excess (20 equivalents) of bromine and of acetic acid in which the oxygen has been removed, and also the instantaneous nature of the bromination reaction, which is difficult to control, are not very compatible with industrial-scale application. The second step of this process calls for the use of solvents such as chloroform, the industrial-scale use of which is not very desirable. The product must be purified by silica column chromatography, a method which is not very suitable for the production of large amounts of product.

3,7-Bis(dimethylamino)phenothiazin-5-ylium chloride is a compound that has been used for a long time as a redox indicator and dye, as an optical revealing agent in biophysical systems, in nanoporous materials as a separating material, and in photoelectrochemical imaging. It is also known for its applications as an antiseptic, and anti-infective, as an antidote and as a diagnostic agent. It has uses in particular in gynecology, neonatology, cancerology, oncology, urology, ophthalmology and gastroenterology, and the reduction of pathogenic contaminants in blood (GB 2 373 787). New uses in the therapeutic field are in the process of being developed, such as the prevention or inhibition of an excessive hemodynamic reaction (WO 03/082296), the treatment of Alzheimer's disease and more generally the treatment of degenerative diseases of the central nervous system (WO 2008/007074).

For these applications, it is necessary to have a methylene blue composition comprising few organic and metal impurities.

Several known processes for preparing methylene blue call for the use of metal reagents (WO 2005/054217; WO 2006/032879) and result in a product contaminated with metal residues in a large amount. The reduction in the amount of these impurities requires fastidious purification steps.

It is limited by the metal-complexing nature of the 3,7-bis(dimethylamino)-phenothiazin-5-ylium molecule.

Methylene blue and its organic impurities: azure A, azure B and azure C, have very close structures which make it difficult to separate them using conventional separation techniques.

Methods for purifying methylene blue, in order to remove therefrom the metal and organic contaminants, have been described (WO 2008/007074; WO 2008/006979). However, the synthesis of crude methylene blue, to which these purification methods are applied, involves the use of toxic reagents such as chromium derivatives.

Consequently, there thus remains the need for a process which makes it possible to directly obtain a 3,7-bis(dimethylamino)phenothiazin-5-ylium halide of high purity, with satisfactory yields, this process not calling for highly toxic reagents such as chromium oxides.

There is in particular the need for a process which makes it possible to prepare methylene blue for use in the therapeutic field by virtue of a process that is simple to carry out, with a high yield and a high degree of purity.

3,7-Bis(dimethylamino)phenothiazin-5-ylium iodide makes it possible to easily obtain, by various methods of conversion, 3,7-bis(dimethylamino)phenothiazin-5-ylium chloride.

The objective of the invention was to develop a novel process for preparing 3,7-bis(dimethylamino)phenothiazin-5-ylium iodide. Such a process makes it possible to obtain 3,7-bis(dimethylamino)phenothiazin-5-ylium chloride or methylene blue, by simple ion exchange or by other known methods that will be described below.

The applicant has sought to develop a process for synthesizing 3,7-bis(dimethylamino)phenothiazin-5-ylium iodide which is rapid, inexpensive, efficient, with a high yield and degree of purity and can be easily extrapolated to the industrial scale.

SUMMARY OF THE INVENTION

The invention relates to a process for preparing 3,7-bis(dimethylamino)-phenothiazin-5-ylium iodide, this process using phenothiazine as starting product and comprising the following steps:
  treating phenothiazine with diiodine,
  treating the reaction medium directly resulting from step a) with dimethylamine.

According to one preferred embodiment, the treatment with diiodine is carried out with an amount of diiodine, relative to the phenothiazine, ranging from 2.5 molar equivalents to 3.5 molar equivalents.

Even more advantageously, the treatment with diiodine is carried out with an amount of diiodine, relative to phenothiazine, ranging from 2.9 molar equivalents to 3.3 molar equivalents.

According to one preferred embodiment, before step b), the reaction medium resulting from step a) is conditioned at a temperature ranging from 5° C. to 50° C., preferably from 10° C. to 45° C., even better still from 20° C. to 35° C.

According to one preferred embodiment, the treatment with dimethylamine is carried out with at least 7 molar equivalents of dimethylamine relative to the phenothiazine.

According to one preferred embodiment, in step a), the solvent is chosen from: an aromatic solvent or acetonitrile, or mixtures thereof, preferably toluene or acetonitrile, or mixtures thereof.

According to one preferred embodiment, in step b), the dimethylamine is introduced into the reaction medium in the form of a solution in water.

According to one preferred embodiment, a precipitate forms at the outcome of the treatment of step b), said precipitate being recovered by filtration.

The invention also relates to the use of the process described above, and in detail below, for producing a composition comprising 3,7-bis(dialkylamino)phenothiazin-5-ylium iodide, wherein the 3,7-bis(dialkylamino)phenothiazin-5-ylium iodide represents at least 95% of the composition, the % being measured by HPLC with detection at 246 nm.

The invention also relates to a process for producing 3,7-bis(dimethylamino)phenothiazin-5-ylium chloride, this process comprising:
  i) producing 3,7-bis(dimethylamino)phenothiazin-5-ylium iodide according to the process described above and in detail below,
  ii) converting the 3,7-bis(dimethylamino)phenothiazin-5-ylium iodide into 3,7-bis(dimethylamino)phenothiazin-5-ylium chloride.

The invention also relates to a process for producing a medicament comprising 3,7-bis(dimethylamino)phenothiazin-5-ylium chloride, this process comprising the production of 3,7-bis(dimethylamino)phenothiazin-5-ylium chloride according to the process described above, and in detail below, and the introduction thereof into a pharmaceutically acceptable medium.

According to one preferred embodiment, the process for producing a medicament relates to the production of a medicament intended for the prevention or treatment of a pathological condition selected from: a tauopathy, a tau protein aggregation disease, Pick's disease, progressive supranuclear palsy (PSP), frontotemporal dementia (FTD), FTD and parkinsonism linked to chromosome 17 (FTDP-17), disinhibition-dementia-parkinsonism-amyotrophy complex (DDPAC), pallido-ponto-nigral degeneration (PPND), guam-ALS syndrome, pallido-nigro-luysian degeneration (PNLD), corticobasal degeneration (CBD), mild cognitive impairment (MCI), skin cancer, melanoma, methemoglobinemia, a viral infection, a bacterial infection, a protozoan infection, a parasite infection, malaria, visceral leishmaniosis, African sleeping sickness, toxoplasmosis, giardiasis, Chagas disease, a hepatitis C virus (HCV) infection, a human immunodeficiency virus (HIV) infection, a West Nile virus (WNV) infection, synucleinopathy, Parkinson's disease (PD), Lewy body dementia (DLB), multiple system atrophy (MSA), drug-induced parkinsonism, pure autonomic failure (PAF), septic shock, excessive hemodynamic reaction, breast cancer, manic-depressive disorders, Alzheimer's disease (AD) and more generally the treatment of degenerative diseases of the central nervous system.

The expression "consists essentially of" followed by one or more characteristics means that components or steps which do not significantly modify the properties and characteristics of the invention can be included in the process or the material of the invention, in addition to the explicitly listed components or steps.

DETAILED DESCRIPTION

The invention relates to a two-step process for converting phenothiazine into 3,7-bis(dimethylamino)phenothiazin-5-ylium iodide carried out in one and same reaction medium.
This conversion process comprises:
  a) treating phenothiazine with diiodine;
  b) treating the reaction medium directly resulting from step a) with dialkylamine.

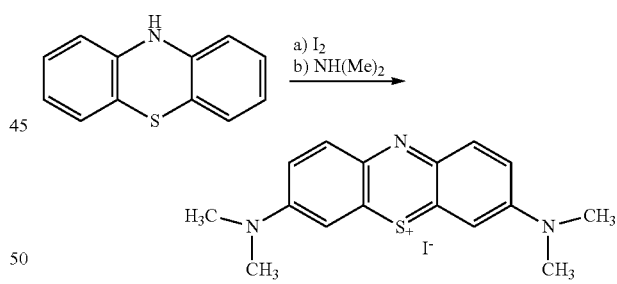

Scheme 1: One-pot conversion of phenothiazine into 3,7-bis(dimethylamino)phenothiazin-5-ylium iodide This preparation process makes it possible to obtain 3,7-bis(dimethylamino)phenothiazin-5-ylium iodide, with a high degree of purity, while at the same time being very simple to carry out and providing high yields.

It is known from the prior art that the addition of diiodine to a phenothiazine produces an oxidation reaction.

The oxidation of phenothiazine with iodine makes it possible to form periodide, an intermediate product of the reaction, which, in the prior processes, is purified and isolated.

The invention relates to a process for preparing 3,7-bis(dimethylamino)phenothiazin-5-ylium iodide which does not require the isolation and purification of the periodide.

Indeed, it has been noted that the isolation and purification of the periodide in an additional step results, after treatment with dimethylamine, in a 3,7-bis(dimethylamino)phenothiazin-5-ylium iodide of relatively unsatisfactory quality and that such a process provides low yields.

The process of the invention is characterized in that the two essential steps are carried out in the same reaction medium. Such a process is also usually referred to as "one-pot", literally "one reactor", which means that the succession of reactions is carried out without complete or partial isolation or purification of the product of step a) before the involvement of step b). The composition of the reaction medium changes over time, but the intermediate products are not isolated and/or purified, only the final product is separated from the reaction medium. In the process of the invention, at least two successive reactions take place, the composition of the reaction medium changes over time, but the phenothiazine periodide is not isolated and/or purified, only the 3,7-bis(dimethylamino)phenothiazin-5-ylium iodide is separated from the reaction medium.

Such a process has the advantage of being easy to carry out and of requiring few manipulations. Usually, one-pot processes have the reputation of producing mixtures that are less pure than those which are carried out with isolation and purification of the intermediates. However, in the present case, surprisingly, it has been noted that the process in two steps a) and b) carried out in one and the same reaction medium results in a product of higher purity than a similar process carried out with isolation and purification of the phenothiazine periodide.

Phenothiazine:

The starting product is phenothiazine which is a commercial product.

Preferably, the phenothiazine used as starting product has an organic purity greater than or equal to 98% (in % of area) measured by high performance liquid chromatography, with detection at 246 nm.

Advantageously, a phenothiazine comprising few or no metal impurities is used. Preferably, a phenothiazine comprising less than 200 ppm of metal contaminants, advantageously less than 100 ppm of metal contaminants, even better still less than 50 ppm of metal contaminants, and even more advantageously less than 20 ppm of metal contaminants, is used.

The term "metal contaminants" is intended to mean all the metals of the periodic table of elements and in particular: Cd, Cr, Hg, Mn, Ni, Sn, Pb, Al, Fe, Cu, Zn, As, Mo, Mg, Ti, V, U, Co. More particularly, the term "metal contaminants" is intended to mean the "heavy" metals and in particular: Al, Cd, Cr, Cu, Sn, Mn, Hg, Mo, Ni, Pb, Zn.

Step a): Treatment of Phenothiazine with Diiodine:

According to the invention, steps a) and b) are carried out in a solvent or a mixture of solvents.

In step a), a single solvent or a mixture of solvents can be used. In step b), the dimethylamine is introduced into the reaction medium in the form of a solution in a solvent which may be identical to or different than that of step a).

The phenothiazine is treated with diiodine, then with dimethylamine, in a solvent, or in a mixture of solvents, which is chosen in particular for its ability to solubilize phenothiazine and diiodine.

Among the solvents that can be used in the process of the invention, mention may be made of: alcohols, such as methanol or ethanol; tetrahydrofuran; aromatic solvents, such as toluene, xylene and ethylbenzene; acetonitrile; mixtures of these solvents.

Preferably, the treatment of phenothiazine with diiodine is carried out in a solvent chosen from aromatic solvents and acetonitrile.

Advantageously, the solvent is chosen from toluene and acetonitrile.

Advantageously, the treatment of phenothiazine with diiodine is carried out with at least 2.5 molar equivalents and at most 3.5 molar equivalents of diiodine relative to the phenothiazine. Outside this range of values, a significant decrease in the 3,7-bis(dimethylamino)phenothiazin-5-ylium iodide yields has been noted. Preferably, the treatment of phenothiazine with diiodine is carried out with at least 2.7 molar equivalents and at most 3.3 molar equivalents of diiodine relative to the phenothiazine, even better still with at least 2.8 molar equivalents and at most 3.2 molar equivalents of diiodine relative to the phenothiazine.

Preferably, the treatment of phenothiazine with diiodine is carried out with approximately three molar equivalents of diiodine relative to the phenothiazine.

According to a first preferred embodiment, step a) is carried out in toluene in the presence of at least 2.5 molar equivalents and at most 3.5 molar equivalents of diiodine relative to the phenothiazine.

Preferably, step a) is carried out in toluene in the presence of at least 2.7 molar equivalents and at most 3.3 molar equivalents of diiodine relative to the phenothiazine, even better still with at least 2.8 molar equivalents and at most 3.2 molar equivalents of diiodine relative to the phenothiazine.

According to a second preferred embodiment, step a) is carried out in acetonitrile in the presence of at least 2.5 molar equivalents and at most 3.5 molar equivalents of diiodine relative to the phenothiazine.

Preferably, step a) is carried out in acetonitrile in the presence of at least 2.7 molar equivalents and at most 3.3 molar equivalents of diiodine relative to the phenothiazine, even better still with at least 2.8 molar equivalents and at most 3.2 molar equivalents of diiodine relative to the phenothiazine.

Preferably, step a) is carried out with stirring at a temperature ranging from ambient temperature to 100° C. Since this step is not exothermic, the reagents and the solvent(s) are introduced into the reactor which is then conditioned at the selected temperature.

Advantageously, the treatment of phenothiazine with diiodine is carried out at a temperature ranging from 30° C. to 90° C., advantageously from 40° C. to 80° C., even better still from 50° C. to 70° C.

Preferably, the total duration of treatment of phenothiazine with diiodine is from 15 minutes to 6 h, advantageously from 30 minutes to 4 h, even better still from 1 h to 3 h.

It is possible to monitor the progression of the reaction by thin layer chromatography or by HPLC (high performance liquid chromatography).

Advantageously, the treatment of phenothiazine with diiodine is carried out:
- at a temperature ranging from 30° C. to 90° C. for a period of from 15 minutes to 6 h,
- preferentially at a temperature ranging from 30° C. to 90° C. for a period of from 30 minutes to 4 h,
- advantageously at a temperature of from 40° C. to 80° C. for a period of from 1 h to 3 h.

Unlike the prior art, the reaction medium obtained at the outcome of this reaction is directly subjected to a treatment with dimethylamine, without partially or totally isolating and/or purifying the intermediate product.

Step b) Treatment of the Reaction Medium with Dimethylamine

Dimethylamine NH(CH$_3$)$_2$, which is advantageously introduced in the form of a solution in a solvent, is added to the reaction medium at the outcome of step a).

The dimethylamine solution may be in a solvent or a mixture of solvents chosen from: water, tetrahydrofuran, methanol, ethanol, a mixture of these solvents.

Preferably, the dimethylamine is introduced into the reaction medium in the form of a solution in water or in tetrahydrofuran or in a mixture of these solvents.

Even more preferentially, the dimethylamine is introduced into the reaction medium in the form of a solution in water.

According to a first preferred embodiment, the reaction medium after the introduction of the dimethylamine comprises a mixture of toluene and water in a volume ratio ranging from 99/1 to 50/50, advantageously from 95/5 to 60/40, even better still from 90/10 to 70/30.

According to a second preferred embodiment, the reaction medium after the introduction of the dimethylamine comprises a mixture of acetonitrile and water in a volume ratio ranging from 99/1 to 50/50, advantageously from 95/5 to 60/40, even better still from 90/10 to 70/30.

Preferably, the treatment with dimethylamine is carried out with at least six molar equivalents of dimethylamine relative to the phenothiazine, advantageously at least seven molar equivalents of dimethylamine relative to the phenothiazine, even more advantageously at least eight molar equivalents of dimethylamine relative to the phenothiazine.

Preferably, the treatment with dimethylamine is carried out with from six to fifteen molar equivalents of dimethylamine relative to the phenothiazine, advantageously from seven to twelve molar equivalents of dimethylamine relative to the phenothiazine, even more advantageously from eight to twelve molar equivalents of dimethylamine relative to the phenothiazine.

The addition of dimethylamine results in an exothermic reaction.

Advantageously, the temperature of the reaction medium is controlled before the introduction of the dimethylamine. Preferably, the temperature of the reaction medium is from 1° C. to 50° C. at the time the dimethylamine is introduced, preferentially it is from 2° C. to 40° C., even better still from 5° C. to 30° C.

The exothermy of the reaction results in an increase in the temperature of the reaction medium for the duration of the introduction of the dimethylamine. After all the dimethylamine has been poured into the reaction medium, the temperature stabilizes. Advantageously, the temperature of the reaction medium is then controlled and maintained at 20-25° C.

Preferably, the reaction medium is then kept stirring and at a temperature ranging from 20 to 25° C. for 20 minutes to 6 h, preferably from 1 h to 5 h, even better still from 2 h to 4 h.

The addition of dimethylamine to the reaction medium results in a change in color of this medium, which goes from brown to dark blue.

According to the invention, after this period of time, the formation of a solid in the reaction medium is observed. It is possible to monitor the progression of the reaction by HPLC.

After the reaction with dimethylamine, it is possible, in order to promote the precipitation of the 3,7-bis(dialkylamino)phenothiazin-5-ylium iodide, to treat the reaction medium by adding another solvent in which it is insoluble or sparingly soluble. Depending on the choice of the solvent in which the reaction was carried out, it is possible to use, a choice of: toluene, tetrahydrofuran, acetonitrile, ethanol, acetone, water or a mixture of these solvents.

According to a first preferred embodiment, the reaction medium comprises toluene and, at the outcome of step b), a solvent is added that is chosen from: tetrahydrofuran, acetonitrile, acetone, ethanol, water or a mixture of these solvents.

According to a second preferred embodiment, the reaction medium comprises acetonitrile and, at the outcome of step b), a solvent is added which is chosen from: tetrahydrofuran, toluene, acetone, ethanol, water or a mixture of these solvents.

The 3,7-bis(dialkylamino)phenothiazin-5-ylium iodide is then isolated from the reaction medium by filtration on a suitable filtration support, which may for example be a sintered glass funnel or filtering cloth.

The fraction retained by the filter is a composition comprising 3,7-bis(dialkylamino)phenothiazin-5-ylium iodide.

The filtrate is eliminated, while the precipitate is washed one or more times with a solvent.

Preferably, the filtration is followed by a step of washing the solid with a solvent which may be chosen from: toluene, tetrahydrofuran, acetonitrile, acetone, ethanol, dichloromethane, water or a mixture of these solvents.

Another subject of the invention is the use of the process described above, for producing 3,7-bis(dimethylamino)phenothiazin-5-ylium iodide with a good chemical purity, in a manner that is reliable, reproducible and applicable to the industrial scale.

The process of the invention gives access to compositions comprising 3,7-bis(dimethylamino)phenothiazin-5-ylium iodide having a 3,7-bis(dimethyl-amino)phenothiazin-5-ylium iodide content of greater than or equal to 85%, preferentially greater than or equal to 90%, even better still greater than or equal to 95%, and advantageously greater than or equal to 98%, as % of area measured in high performance liquid chromatography (HPLC) according to the method described in the European Pharmacopeia 8.6 (published in 2015) for 3,7-bis(dimethylamino)-phenothiazin-5-ylium chloride.

The process of the invention gives access to compositions comprising 3,7-bis(dimethylamino)phenothiazin-5-ylium iodide having a 3-(dimethylamino)-7-(methylamino)phenothiazin-5-ylium iodide less than or equal to 3%, preferentially less than or equal to 2%, even better still less than or equal to 1%, as % of area measured by high performance liquid chromatography (HPLC) according to the method described in the European Pharmacopeia 8.6 (published in 2015) for 3,7-bis(dimethylamino)phenothiazin-5-ylium chloride.

The process of the invention thus gives access to 3,7-bis(dialkylamino)phenothiazin-5-ylium iodide of high purity and with satisfactory yields.

The process of the invention uses starting materials and solvents which are not particularly dangerous. It calls for steps that can be easily extrapolated to a larger scale. Consequently, this process can be industrialized without any difficulty linked to safety, to yield or to quality of the product.

These qualitites are essential for obtaining 3,7-bis(dimethylamino)-phenothiazin-5-ylium chloride, also known as methylene blue, of satisfactory quality and with high yields.

This process is fast and calls for inexpensive and non-toxic starting materials, and consequently its application to the industrial scale may make it possible to replace the current processes for producing methylene blue.

A subject of the invention is also a process for producing 3,7-bis(dimethylamino)phenothiazin-5-ylium chloride. This process comprises the production of 3,7-bis(dimethylamino) phenothiazin-5-ylium iodide according to the process described above and an additional step of converting the 3,7-bis(dimethylamino)phenothiazin-5-ylium iodide into 3,7-bis(dimethylamino)phenothiazin-5-ylium chloride.

According to a first embodiment, the conversion of the iodide into 3,7-bis(dimethylamino)phenothiazin-5-ylium chloride is carried out by ion exchange. The exchange of the iodide ion to a chloride ion is carried out by virtue of an ion exchange resin such as, for example, an Amberlite® resin, in particular an Amberlite® IRA958 resin. Such a step is well known to those skilled in the art; reference may in particular be made to Anita Gollmer, et al. Photochem. Photobiol. Sci.; vol. 14, n°2, 1 Jan. 2015, p. 335-351, for details of the operating conditions.

According to a second embodiment, the conversion of the iodide into 3,7-bis(dimethylamino)phenothiazin-5-ylium chloride is carried out by implementing the process described in application WO 2008/006979, in particular in the experimental section.

Briefly, 3,7-bis(dimethylamino)phenothiazin-5-ylium iodide is converted into 3,7-bis(dimethylamino)-10-benzoylphenothiazine. This is then purified by filtration on silica and washing with dichloromethane. The purified product is debenzoylated and oxidized by treatment with a quinone, for instance 2,3-dichloro-5,6-dicyano-1,4-benzoquinone (DDQ). The 3,7-bis(dimethylamino)phenothiazine is then salified with HCl, neutralized and optionally recrystallized. A 3,7-bis(dimethylamino)phenothiazin-5-ylium chloride of high purity is thus obtained, having used, as starting product, a phenothiazine which is a commercial product, the synthesis of which does not call for the use of highly toxic reagents such as chromium derivatives which are commonly used for producing crude-quality methylene blue.

Moreover, during the benzoylation reaction, 3,7-bis(dimethylamino)-phenothiazin-5-ylium iodide is preferentially benzoylated, whereas 3-dimethylamino-7-methylaminophenothiazin-5-ylium iodide, 3,7-bis(methylamino)phenothiazin-5-ylium iodide and 3-methylaminophenothiazin-5-ylium iodide are very weakly benzoylated. In addition, when they are benzoylated, 3-dimethylamino-7-methylaminophenothiazin-5-ylium iodide, 3,7-bis(methylamino)phenothiazin-5-ylium iodide and 3-methylaminophenothiazin-5-ylium iodide are also polybenzoylated in not insignificant proportions. These specific characteristics of the most frequent contaminants of 3,7-bis(dimethylamino)phenothiazin-5-ylium iodide facilitate the removal of these contaminants during the purification of the benzoylated form of 3,7-bis(dimethylamino)phenothiazin-5-ylium iodide. Thus, the process of the invention, optionally followed by the process described in application WO 2008/006979, gives access to a methylene blue substantially free of its usual contaminants: azure B, azure A and azure C.

According to a third embodiment, the conversion of the iodide into 3,7-bis(dimethylamino)phenothiazin-5-ylium chloride is carried out by implementing the process described in application WO 2008/007074, in particular in the experimental section.

This process comprises the acetylation of 3,7-bis(dimethylamino)phenothiazin-5-ylium iodide to give N-3,7-bis(dimethylamino)-10-acetylphenothiazine. This is then purified by recrystallization from ethanol. The purified product is deacetylated and oxidized by treatment with $FeCl_3$. 3,7-Bis(dimethylamino)phenothiazinium chloride is optionally recrystallized from water at acid pH.

The process of the invention gives access to compositions comprising 3,7-bis(dimethylamino)phenothiazin-5-ylium chloride (methylene blue) having a 3,7-bis(dimethylamino) phenothiazin-5-ylium chloride content of greater than or equal to 97%, preferentially greater than or equal to 98%, as % of area measured by high performance liquid chromatography (HPLC) according to the method of the European Pharmacopeia 8.6 (edition of January 2012).

The process of the invention gives access to compositions comprising 3,7-bis(dimethylamino)phenothiazin-5-ylium chloride having a 3-dimethylamino-7-methylaminophenothiazin-5-ylium chloride (azure B) content of less than or equal to 2%, preferentially less than or equal to 1%, by % of area measured by high performance liquid chromatography (HPLC) according to the method of the European Pharmacopeia 8.6 (published in 2015).

The process of the invention also gives access to compositions comprising 3,7-bis(dimethylamino)phenothiazin-5-ylium chloride comprising few or no metal impurities. The process of the invention gives in particular access to compositions comprising 3,7-bis(dimethylamino)phenothiazin-5-ylium chloride and comprising less than 200 ppm of metal contaminants, advantageously less than 100 ppm of metal contaminants, even better still less than 50 ppm of metal contaminants, and even more advantageously less than 20 ppm of metal contaminants. The metal content is measured according to the method of the European Pharmacopeia 8.6 (published in 2015).

The term "metal contaminants" is intended to mean all the metals of the periodic table of elements and in particular: Cd, Cr, Hg, Mn, Ni, Sn, Pb, Al, Fe, Cu, Zn, As, Mo, Mg, Ti, V, U, Co. More particularly, the term "metal contaminants" is intended to mean the "heavy" metals and in particular: Al, Cd, Cr, Cu, Sn, Mn, Hg, Mo, Ni, Pb, Zn.

The process of the invention makes it possible to obtain compositions comprising 3,7-bis(dimethylamino)phenothiazin-5-ylium chloride which are substantially free of 3,7-bis(dimethylamino)phenothiazin-5-ylium iodide.

3,7-Bis(dimethylamino)phenothiazin-5-ylium chloride, also known as methylene blue, has been used for decades in the treatment of various infections. It is used as an antiseptic, an anti-infective, as an antidote as treatment for methemoglobinemia and as a diagnostic agent.

Its antiviral activity has recently been demonstrated and it could be used for the production of a medicament intended for use in treating: a tauopathy, a tau protein aggregation disease, Pick's disease, progressive supranuclear palsy (PSP), frontotemporal dementia (FTD), FTD and parkinsonism linked to chromosome 17 (FTDP-17), disinhibition-dementia-parkinsonism-amyotrophy complex (DDPAC), pallido-ponto-nigral degeneration (PPND), Guam-ALS syndrome, pallido-nigro-luysian degeneration (PNLD), corticobasal degeneration (CBD), mild cognitive impairment (MCI), skin cancer, melanoma, methemoglobinemia, a viral infection, a bacterial infection, a protozoan infection, a parasite infection, malaria, visceral leishmaniosis, African sleeping sickness, toxoplasmosis, giardiasis, Chagas disease, a hepatitis C virus (HCV) infection, a human immunodeficiency virus (HIV) infection, a West Nile virus (WNV) infection, synucleinopathy, Parkinson's disease (PD), Lewy body dementia (DLB), multiple system atrophy (MSA), drug-induced parkinsonism, pure autonomic failure (PAF), septic shock, excessive hemodynamic reaction, breast cancer, manic-depressive disorders, Alzheimer's disease (AD) and more generally the treatment of degenerative diseases of the central nervous system.

The 3,7-bis(dimethylamino)phenothiazin-5-ylium chloride could also be used in cosmetics or for products intended for ophthalmic application.

For all these therapeutic applications, and in particular in a context of prevention and treatment of Alzheimer's disease, and more generally of treatment of degenerative diseases of the central nervous system, which require a recurrent administration of methylene blue during prolonged periods, it is necessary to have a methylene blue which has a high degree of purity and very few metal impurities.

A subject of the invention is also a process for producing a medicament, this process comprising the production of 3,7-bis(dimethylamino)phenothiazin-5-ylium chloride and the introduction thereof into a pharmaceutically acceptable medium.

Said medicament may be in any form suitable for its use in these applications.

In particular, mention may be made of: in the form of a tablet or of a gel capsule comprising from 1 to 500 mg of methylene blue; in the form of an aqueous solution comprising methylene blue at a concentration ranging from 0.05% to 2% in g/l.

Such compositions comprise, in addition to the methylene blue, excipients well known to those skilled in the art, such as for example citric acid and/or citrates, a phosphate buffer, polymers, cellulose derivatives, lipids.

In medical applications, the methylene blue obtained by means of the process of the invention has the advantage of a high purity, which avoids introducing into the body materials that are needless for the application.

The efficiency of the process of the invention makes it possible to access a product that is lower in cost, is easily reproducible and is applicable to the industrial scale.

Experimental Section

I—Materials and Methods:
1) Starting Materials and Equipment:
The diiodine was purchased from the company TCI.
The phenothiazine was purchased from the company ALFA AESAR, ACROS ORGANICS.
The dimethylamine was purchased:
from the company ACROS ORGANICS under the trade reference Dimethylamine 40% wt solution in water
from the company ACROS ORGANICS under the trade reference Dimethylamine 2M solution in THF
from the company TCI under the trade reference Dimethylamine, 2M solution in MeOH.
2) Analysis Method:
HPLC/MS
Method: Pharmacopeia EP 8.6 published in 2015
Apparatus: HPLC Agilent 1260+MS Agilent 6120
Column: Waters XBridge Phenyl 100×4.6–3.5 µm
Detection: 246 nm
Sample concentration: 1000 ppm
Sample dissolution solvent: TFA 0.1% aq./ACN (70/30)
Elution solvent: acetonitrile/0.1% (v/v) trifluoroacetic acid in water
Ionization source for the MS: Electrospray (ESI)
Analyzer for the MS: simple quadrupole
Detector for the MS: electron multiplier
Computer system for the data processing: Agilent Chemstation Open Lab II—Protocols:

Example 1 (Comparative)

Two-Step Synthesis of 3,7-bis(dimethylamino)phenothiazin-5-ylium iodide (according to Anita Gollmer, et al., Photochem. Photobiol. Sci.; 2014; DOI:10.1039/C4PP00309H; p. 1-47)

1) Synthesis of phenothiazin-5-ylium tetraiodide (1294-X15)

10 g of phenothiazine (50 mmol, 1.0 eq.) and 200 ml of dichloromethane are introduced into a 500 ml three-necked flask. The mixture is stirred at ambient temperature.

38.3 g of diiode (150 mmol, 3.0 eq.) are then added with stirring, and at ambient temperature.

The reaction medium is then kept stirring at ambient temperature for 2 h.

The reaction medium is then filtered on a frit, pore 3.

The precipitate is washed with 20 ml of dichloromethane, then filtered on a frit, pore 3.

The solid is dried in an oven at 40° C.

31.6 g of black-colored, crude phenothiazine tetraiodide are obtained. The yield is 89.5%.

2) Conversion of the phenothiazine tetraiodide into 3,7-bis(dimethylamino)-phenothiazin-5-ylium iodide (1294-Y19)

4.5 g of phenothiazine periodide (7.1 mmol, 1.0 eq.) are introduced into a 500 ml three-necked flask and dissolved in a mixture of methanol (180 ml) and dichloromethane (22.5 ml), with stirring and at ambient temperature.

35.5 ml of a 2N dimethylamine solution in methanol (71.0 mmol, 10.0 eq.) are run in, with stirring, over the course of 50 min, conditioned at a temperature of between 20° C. and 25° C.

The reaction medium is then kept stirring at ambient temperature for 6 h at 22° C.

The reaction medium is then filtered on a frit, pore 4.

The product is obtained in the form of a powder and dried in a ventilated oven at 40° C.

1.39 g of a black-colored solid are obtained, and the reaction yield is 47.7%, which corresponds to 42.7% relative to the total amount of phenothiazine used in the process.

The product is analyzed by the HPLC/MS method described above.

The 3,7-bis(dimethylamino)phenothiazin-5-ylium iodide content in the solid obtained is 85.4%. Among the impurities, phenothiazine dimers in an amount of 11.11% were identified.

Example 2

One-Step Synthesis of 3,7-bis(dimethylamino)phenothiazin-5-ylium iodide (1294-AD2)

88 g of diiodine (346.2 mmol, 3.0 eq.) and 1.15 l of toluene are mixed in a 2 l three-necked flask. 23 g of phenothiazine (115.4 mmol, 1.0 eq.) are added, with stirring and at ambient temperature.

The reaction medium is then kept stirring at ambient temperature for 3 h.

575 ml of a 2N dimethylamine solution in methanol (1154 mmol, 10.0 eq.) are then rapidly added (less than one minute) to the reaction medium conditioned at a temperature of 20 to 25° C., with stirring.

The reaction medium is then kept stirring at ambient temperature for 2 h 30.

The reaction medium is then filtered on a frit, pore 3.

The precipitate is washed once with toluene, then filtered on a frit, pore 3.

The solid is dried in a Rotavapor® at 40° C.

40.9 g of a black-colored product are obtained; the yield obtained is 86%.

The product is analyzed by the HPLC/MS method described above.

The 3,7-bis(dimethylamino)phenothiazin-5-ylium iodide content is 85%.

Example 3

One-Step Synthesis of
3,7-bis(dimethylamino)phenothiazin-5-ylium iodide
(1294-AD68)

5 g of phenothiazine (25.1 mmol, 1.0 eq.) and 100 ml of acetonitrile are added to a 250 ml three-necked flask. The reaction medium is heated to 40° C.

19.7 g of diiodine (77.8 mmol, 3.1 eq.) are added and the heating is continued for 2 h.

The reaction medium is cooled to 25° C.

31.8 ml of dimethylamine in the form of a 40% by weight solution in $H_2O$ (250.9 mmol, 10.0 eq.) are introduced while keeping the reaction medium between 25 and 30° C.

The medium is left to stir for 2 h at 25° C.

The medium is diluted with 100 ml of acetone and is left to stir for 30 min at 25° C.

The reaction medium is filtered on a frit, pore 3.

The precipitate is washed four times with 20 ml of acetone.

The solid is dried overnight in a ventilated oven at 40° C.

6.9 g of a black-colored product are obtained; the yield obtained is 67%.

The product is analyzed by HPLC/MS according to the method described above; the purity is 94.4%.

Example 4

One-Step Synthesis of
3,7-bis(dimethylamino)phenothiazin-5-ylium iodide
(AD97)

The process is carried out as in example 3, with the following difference: the dimethylamine is introduced while keeping the reaction medium between 10 and 15° C.

4.28 g of a black-colored product are obtained; the yield obtained is 41%.

The product is analyzed by HPLC/MS according to the method described above; the purity is 98.3%.

Example 5

One-Step Synthesis of 3,7-bis(dimethylamino)phenothiazin-5-ylium iodide (AD98)

The process is carried out as in example 3, with the following difference: the dimethylamine is introduced while keeping the reaction medium between 35 and 40° C.

6.21 g of a black-colored product are obtained; the yield obtained is 60%.

The product is analyzed by HPLC/MS according to the method described above; the purity is 88.1%.

Example 6

One-Step Synthesis of
3,7-bis(dimethylamino)phenothiazin-5-ylium iodide
(AD99)

The process is carried out as in example 3, with the following difference: the dimethylamine is introduced while keeping the reaction medium between 60 and 70° C.

4.82 g of a black-colored product are obtained; the yield obtained is 47%.

The product is analyzed by HPLC/MS according to the method described above; the purity is 73.3%.

Example 7

One-Step Synthesis of
3,7-bis(dimethylamino)phenothiazin-5-ylium iodide
(AD55)

5 g of phenothiazine (25.1 mmol, 1.0 eq.) and 100 ml of acetonitrile are introduced into a 500 ml three-necked flask. The reaction medium is heated to 40° C.

19.1 g of diiodine (75.3 mmol, 3.0 eq.) are added and the heating is continued for 2 h.

The reaction medium is cooled to 18° C.

31.8 ml of dimethylamine in the form of a 40% by weight solution in $H_2O$ (250.9 mmol, 10.0 eq.) are introduced over the course of 5 min. The reaction is exothermic and, at the end of the addition, a reaction medium temperature of 24° C. is observed.

The medium is left to stir for 2 h at ambient temperature.

The medium is diluted with 100 ml of acetone and is left to stir for 30 min at ambient temperature.

The precipitate is filtered off on a frit, pore 3, and washed with acetone.

The solid is dried in a Rotavapor® at 40° C.

6.2 g of a black-colored product are obtained; the yield obtained is 60%.

The product is analyzed by HPLC/MS according to the method described above; the purity is 96.2%.

Example 8

One-Step Synthesis of
3,7-bis(dimethylamino)phenothiazin-5-ylium iodide
(AD62)

5 g of phenothiazine (25.1 mmol, 1.0 eq.) and 100 ml of acetonitrile are introduced into a 500 ml three-necked flask. The reaction medium is heated to 40° C.

25.5 g of diiodine (100.4 mmol, 4.0 eq.) are added and the heating is continued for 2 h.

The reaction medium is cooled to 20-25° C.

31.8 ml of dimethylamine in the form of a 40% by weight solution in $H_2O$ (250.9 mmol, 10.0 eq.) are introduced over the course of 5 minutes. The reaction is exothermic and, at the end of the addition, a reaction medium temperature T<30° C. is observed.

The medium is left to stir for 2 h at ambient temperature.

The medium is diluted with 100 ml of acetone and is left to stir for 30 min at ambient temperature.

The precipitate is filtered off on a frit, pore 3, and washed with acetone.

The solid is dried in a Rotavapor® at 40° C.

4.0 g of a black-colored product are obtained; the yield obtained is 39%.

The product is analyzed by HPLC/MS according to the method described above; the purity is 98.1%.

Example 9

Synthesis of 3,7-bis(dimethylamino)-10-benzoylphenothiazine (1294-AD86)

100 g of phenothiazine (502 mmol, 1.0 eq.), 394.8 g of diiodine (1555 mmol, 3.1 eq.) and 2 l of acetonitrile are introduced into a 6-liter reactor.

The reaction medium is heated at 40° C. for 2 h.

The reaction medium is cooled to 25° C.

633 ml of dimethylamine in the form of a 40% by weight solution in $H_2O$ (5020 mmol, 10.0 eq.) are introduced while keeping the reaction medium between 25 and 30° C.

The medium is left to stir for 2 h at 25° C.

The medium is diluted with 2 l of acetone and is left to stir for 30 min at 25° C.

The precipitate obtained is filtered off on a frit, pore 3, then washed 4 times with 400 ml of acetone.

The solid is dried overnight in a ventilated oven at 40° C.

128.4 g of a black-colored product are obtained; the yield obtained is 62.2%.

The product is analyzed by HPLC/MS according to the method described above; the purity is 95.5%.

Example 10

Synthesis of 3,7-bis(dimethylamino)-10-benzoylphenothiazine (1294-Z18)

30 g of 3,7-bis(dimethylamino)phenothiazin-5-ylium iodide (72.9 mmol, 1.0 eq.) prepared in example 9 are introduced into 600 ml of water, in a 2 l three-necked flask. The mixture is stirred under an $N_2$ stream until complete dissolution is obtained, and is then cooled to 12° C. 44.8 g of 85% sodium hydrosulfite (218.7 mmol, 3.0 eq.) are then added to the solution over the course of 5 min and with stirring.

The reaction medium is stirred at 12° C. for 30 min. 58.32 g of an aqueous 30% sodium hydroxide solution (437.4 mmol, 6.0 eq.) are then added over the course of 10 min. 50.8 ml of benzoyl chloride (437.4 mmol, 6.0 eq.) are added to the reaction medium over the course of 25 min.

The reaction medium is then stirred for 2 h at 12° C. 600 ml of dichloromethane are added, the reaction medium is stirred for a few minutes, then 150 ml of an aqueous 30% sodium hydroxide solution are added and the resulting mixture is left to stir for 1 h at 12° C.

The reaction medium is extracted in a 2 l separating funnel under $N_2$. The aqueous phase is extracted twice with 300 ml of dichloromethane. The organic phase is washed twice with 150 ml of an aqueous 1N sodium hydroxide solution, passed over silica and then evaporated under vacuum. The solid is dissolved in 300 ml of ethanol, and the solution is placed at −20° C. for 45 min. The precipitate is filtered off on a frit, pore 3, washed with ice-cold ethanol and then dried overnight in a ventilated oven at 40° C.

The quantitative determination of the iodine is carried out by ICP/MS. The product obtained contains 1203 ppm of residual iodine.

The metal impurities are analyzed by inductively coupled plasma mass spectrometry, provided with a collision cell (CCT mode). Indium is used as internal standard. Gold is used as mercury stabilizer. A mineralization of the samples is carried out under high pressure with a laboratory microwave oven. The method used is a metered-addition methodology.

The results are reported in the table below:

| Parameter | Result |
| --- | --- |
| Ruthenium | <0.03 ppm |
| Rhodium | <0.03 ppm |
| Cadmium | <0.03 ppm |
| Iridium | <0.03 ppm |
| Mercury | <0.03 ppm |
| Chromium | 1.0 ppm |
| Manganese | <0.15 ppm |
| Nickel | <0.15 ppm |
| Tin | <0.15 ppm |
| Lead | <0.15 ppm |
| Aluminum | <1.2 ppm |
| Iron | <1.2 ppm |
| Copper | <0.6 |
| Zinc | <0.6 |
| Arsenic | <0.15 |
| Molybdenum | <0.15 |

Example 11

Synthesis of 3,7-bis(dimethylamino)phenothiazin-5-ylium chloride (1294-AG10)

Debenzoylation:

In a 500 ml three-necked flask, 5 g of 3,7-bis(dimethylamino)-10-benzoylphenothiazine (12.8 mmol, 1.0 eq.) obtained in example 10 are introduced into 200 ml of acetonitrile. The reaction medium is cooled to −20° C. A solution of 2.97 g of 2,3-dichloro-5,6-dicyano-1,4-benzoquinone (DDQ) (13.1 mmol, 1.02 eq.) in 13.4 ml of acetonitrile is prepared and is conditioned at −20° C.

The cold solution of DDQ is then poured into the three-necked flask and left to stir for 3 h at −20° C. 50 ml of ethyl acetate (EA) are added and the resulting mixture is left to stir for 30 min at −20° C. The reaction medium is filtered on a frit, pore 3, then washed twice with 10 ml of ethyl acetate. The precipitate obtained is washed with 50 ml of an EA/THF mixture (25/75), and drained.

Salification:

The solid obtained is taken up in 40 ml of EA. The mixture is cooled to −20° C. and 39 ml of ethyl acetate/HCl (4.3M) (165.12 mmol, 12.9 eq.) are rapidly added. The reaction medium is left to stir for 3 h at −20° C. The precipitate obtained is filtered off on a frit, pore 3. The solid obtained is taken up in 75 ml of ethyl acetate. The mixture is stirred for 30 min at −20° C. then filtered on a frit, pore 3.

Neutralization:

A measurement of the pH is carried out on 100 mg of precipitate in 20 ml of water, then the pH is adjusted to 3.8 with 200 μL of 0.2M NaOH. The product obtained is taken up in 50 ml of acetone and then cooled to −15° C. 2.3 ml of 2M NaOH, volume previously determined, are added and then the resulting mixture is stirred for 2 h at −15° C. The precipitate obtained is filtered off on a frit, pore 3. The solid is taken up in 20 ml of acetone. The medium is stirred for 30 min at −15° C., filtered on a frit, pore 3, and then a measurement of the pH is carried out under the same conditions as previously. The precipitate is dried overnight in a ventilated oven at 40° C.

Purification and Hydration:

In a 100 ml three-necked flask, 2.67 g of salified methylene blue are introduced into 43 ml of a DCM/EtOH mixture (50/50). The medium is heated to 43° C. with stirring and then hot-filtered on a frit, pore 3. 1.33 ml of water are added to the filtrate and then the dichloromethane is evaporated off under vacuum. 75 ml of ethyl acetate are added to the medium cooled to −20° C., then left to stir overnight. The precipitate obtained is filtered off on a frit, pore 3, then reslurried in 40 ml of a THF/EA solution (75/25). After filtration and drying, for two days in an oven at 40° C., 1.45 g of methylene blue are obtained.

The quantitative determination of the iodines is carried out by ion-exchange chromatography. The product obtained contains less than 0.015 ppm of residual iodide.

The invention claimed is:

1. A process for preparing 3,7-bis(dimethylamino)phenothiazin-5-ylium iodide, the process using phenothiazine as a starting product and comprising the following steps:
   a) treating phenothiazine with diiodine in the presence of a solvent, wherein in step a), the solvent is chosen from: an aromatic solvent or acetonitrile, or mixtures thereof; and
   b) treating the reaction medium directly resulting from step a) with dimethylamine.

2. The process as claimed in claim 1, wherein the treatment with diiodine is carried out with an amount of diiodine, relative to the phenothiazine, that is in a range of from 2.5 molar equivalents to 3.5 molar equivalents.

3. The process as claimed in claim 1, wherein, before step b), the reaction medium resulting from step a) is conditioned at a temperature that is in a range of from 5° C. to 50° C.

4. The process as claimed in claim 1, wherein the treatment with dimethylamine is carried out with at least 7 molar equivalents of dimethylamine relative to the phenothiazine.

5. The process as claimed in claim 1, wherein in step a), the solvent is chosen from: toluene or acetonitrile, or mixtures thereof.

6. The process as claimed in claim 1, wherein, in step b), the dimethylamine is introduced into the reaction medium in a form of a solution in water.

7. The process as claimed in claim 1, wherein a precipitate forms at the outcome of the treatment of step b), and the precipitate is recovered by filtration.

8. The process as claimed in claim 1, wherein the phenothiazine used as the starting product has an organic purity greater than or equal to 98% measured by high performance liquid chromatography, with detection at 246 nm.

9. The process as claimed in claim 1, wherein the phenothiazine used as the starting product comprises less than 20 ppm of metal contaminants.

10. A process for producing a composition comprising 3,7-bis(dialkylamino)phenothiazin-5-ylium iodide, the process comprising the process for preparing the 3,7-bis(dimethylamino)phenothiazin-5-ylium iodide as claimed in claim 1, wherein in the composition, the 3,7-bis(dialkylamino)phenothiazin-5-ylium iodide represents at least 95% of the composition, and the % is measured by HPLC with detection at 246 nm.

11. A process for producing 3,7-bis(dimethylamino)phenothiazin-5-ylium chloride, the process comprising:
   a) producing the 3,7-bis(dimethylamino)phenothiazin-5-ylium iodide according to the process as claimed in claim 1, and
   b) converting the 3,7-bis(dimethylamino)phenothiazin-5-ylium iodide into 3,7-bis(dimethylamino)phenothiazin-5-ylium chloride.

12. A process for producing a composition having a 3,7-bis(dimethylamino)phenothiazin-5-ylium chloride content of greater than or equal to 97% as % of area measured by high performance liquid chromatography with detection at 246 nm, the process comprising producing the 3,7-bis(dimethylamino)phenothiazin-5-ylium chloride according to the process as claimed in claim 11.

13. A process for producing a composition comprising less than 20 ppm of metal contaminants, measured by inductively coupled plasma mass spectrometry, the process comprising producing the 3,7-bis(dimethylamino)phenothiazin-5-ylium chloride according to the process as claimed in claim 11.

14. A process for producing a medicament comprising 3,7-bis(dimethylamino)phenothiazin-5-ylium chloride, the process comprising producing the 3,7-bis(dimethylamino)phenothiazin-5-ylium chloride according to the process as claimed in claim 11, and introducing the 3,7-bis(dimethylamino)phenothiazin-5-ylium chloride into a pharmaceutically acceptable medium.

15. The process as claimed in claim 14, wherein the medicament is intended for the treatment of a pathological condition selected from: a tauopathy, a tau protein aggregation disease, mild cognitive impairment (MCI), methemoglobinemia, a viral infection, a bacterial infection, a parasite infection, malaria, a hepatitis C virus (HCV) infection, a human immunodeficiency virus (HIV) infection, a West Nile virus (WNV) infection, Parkinson's disease (PD), septic shock, Alzheimer's disease (AD), and degenerative diseases of the central nervous system.

\* \* \* \* \*